United States Patent [19]
Jasch

[11] Patent Number: 5,398,405
[45] Date of Patent: Mar. 21, 1995

[54] MICROCONNECTORS ELECTRIC SUPPLY LEADS USING THEM AND METHOD OF MANUFACTURE

[75] Inventor: Ingolf Jasch, Leichlingen, Germany

[73] Assignee: Schwarz Pharma AG, Monheim, Germany

[21] Appl. No.: 177,924

[22] Filed: Jan. 6, 1994

Related U.S. Application Data

[62] Division of Ser. No. 973,704, Nov. 9, 1992, Pat. No. 5,325,584.

[30] Foreign Application Priority Data

Jul. 14, 1992 [DE] Germany ............... 42 23 152.3

[51] Int. Cl.$^6$ .............................................. H01R 4/02
[52] U.S. Cl. ...................................... 29/876; 439/736
[58] Field of Search ............... 29/858, 876, 877, 878; 156/305, 293, 294; 264/272.11, 272.12; 174/76, 77 R; 439/606, 692, 694, 695, 682, 736, 936

[56] References Cited

U.S. PATENT DOCUMENTS

| | | | |
|---|---|---|---|
| 3,195,017 | 7/1965 | Callahan | 317/99 |
| 3,522,575 | 8/1970 | Watson et al. | |
| 3,772,774 | 11/1973 | Knippenberg et al. | 29/878 |
| 3,893,233 | 7/1975 | Glover | 29/628 |
| 4,219,027 | 8/1980 | Lund | 128/642 |
| 4,378,631 | 4/1983 | Head et al. | 29/825 |
| 4,519,662 | 5/1985 | Riley et al. | |
| 4,913,673 | 4/1990 | Kobler | 439/736 |
| 5,194,021 | 3/1993 | Oba et al. | 439/936 X |

FOREIGN PATENT DOCUMENTS

| | | |
|---|---|---|
| 1050853 | 2/1959 | Germany . |
| 1056221 | 4/1959 | Germany . |
| 1128501 | 4/1962 | Germany . |
| 2625893 | 8/1980 | Germany . |
| 3331620 | 3/1984 | Germany . |
| 2629259 | 10/1984 | Germany . |
| 3309788 | 11/1984 | Germany . |
| 3417811 | 10/1985 | Germany . |
| 3729546 | 3/1988 | Germany . |
| 0056881 | 2/1990 | Japan . |
| 1042066 | 9/1966 | United Kingdom . |
| 2046533 | 11/1980 | United Kingdom . |

Primary Examiner—Khiem Nguyen
Attorney, Agent, or Firm—Marshall, O'Toole, Gerstein, Murray & Borun

[57] ABSTRACT

A device for producing a micro connection element 24, 30, the device comprising a cylindrical outer sleeve 1, a cylindrical central element 2 arranged coaxially in the outer sleeve 1, a plurality of cylindrical spacers 3 arranged between the outer sleeve 1 and the central element 2; the spacers 3 respectively arranged between two neighboring assembly elements 4 which are in contact with the neighboring spacers 3, the central element 2 and the outer sleeve 1; the assembly elements 4 can be microplug pins having a length such that they extend out of the arrangement comprising outer sleeve 1, central element 2 and spacers 3 so that the pins can support sleeves for making a microcoupling or female connection element, or the assembly elements 4 can be bushes into which microplug pins can be inserted, with a sleeve being joined to the outer end of each pin for receiving an electric wire, to thereby make a microplug or male connector; the microcoupling and microplug can be used on the ends of an electric supply lead 32 which can be at least partially implanted in a human or animal body and connected to a medical instrument.

8 Claims, 3 Drawing Sheets

MICROCONNECTORS ELECTRIC SUPPLY LEADS USING THEM AND METHOD OF MANUFACTURE

This is a Divisional of U.S. patent application Ser. No. 07/973,704, filed Nov. 9, 1992, now U.S. Pat. No. 5,325,584.

The invention provides a device and process for producing micro plug-in connection elements, as well as an electric supply lead having at least one micro plug-in connection element.

More particularly, the invention relates to a device and a process for producing a micro plug-in connection element as well as an electric supply lead having at least one micro plug-in connection element, which can be partially or wholly implanted in or placed on a living body, in particular for supplying electric energy to an instrument implanted in a human or animal and for making measurements in human or veterinary medicine.

BACKGROUND OF THE INVENTION

German Offenlegungsschrift 3,331,620 discloses an implantable plug-in connection which comprises a plug element and a coupling element and which serves as a means for connection to an implanted medical instrument. This connection has a receptacle with a housing and a coupling which is compression-molded from plastic and is integral with the said housing. Connected to the coupling are the plug elements, to which the electrode leads are connected. The coupling has a plurality of electric terminal parts and an opening for receiving a fastening screw, by which the plug element can be fastened to the coupling.

The space requirement and weight of this plug-in connection is very high because of the number of components. Therefore, major surgery is necessary to introduce or attach these plug-in connections. In addition, the implanted plug-in connection gives the person carrying or having an unpleasant and distressful feeling. Added to this is the fact that the known plug-in connection can trigger off rejection reactions in the body.

It is also known in the prior art to supply electrical power to implanted medical instruments, such as for example cardiac catheters, via an electric supply lead which extends out of the body, and to receive measured electric signals via this supply lead. For this purpose, the supply lead end protruding out of the body is provided with a plug (male connector) or a coupling (female connector). Since the plugs or couplings used up until now are relatively heavy and large, there is the permanent risk of the patient becoming caught by the plug or the coupling and tearing open the incision in the skin through which the supply lead protrudes. Since the supply lead is not fastened on the skin of the patient, for example a test animal, it can happen furthermore that a tensile force exerted on the supply lead causes the cardiac catheter to be pulled out of its position, so that precise measurements are no longer possible and there is a risk of injury. In addition, with virtually every movement of the patient there is a relative movement between skin and supply lead. Due to the constant friction caused as a result, the incision in the skin cannot heal.

SUMMARY OF THE INVENTION

The invention is based on the object of providing a device and a process for producing a biocompatible implantable micro plug-in connection element of lowest weight and smallest dimensions as well as an electric supply lead having at least one micro plug-in connection element. By "micro plug-in connection" is meant a connection formed by plugging a microplug (male connector) into a microcoupling (female connector). Also, a "micro plug-in connection element" can be a microplug or a microcoupling.

This object is achieved by a device for producing a micro plug-in connection element which comprises a cylindrical outer sleeve, a cylindrical central element arranged coaxially in the outer sleeve, a plurality of cylindrical spacers arranged between the outer sleeve and the central element, and cylindrical assembly elements, which are in each case arranged between two neighboring spacers and are in contact with the neighboring spacers, the central element and the outer sleeve. The assembly elements project here out of the arrangement comprising outer sleeve, central element and spacers.

The device according to the invention for producing a micro plug-in connection element can be used to produce microplugs having a plurality of plug elements or microcouplings having a plurality of coupling elements which are of very low weight and small dimensions. In addition, the coupling or plug elements of the micro plug-in connection elements produced can be aligned exactly.

The weight of a four-pin micro plug-in connection made from a microcoupling and a microplug produced by the device according to the invention can be less than 0.2 g. The entire micro plug-in connection comprising a microcoupling and a microplug is in this case less than 6 mm long. Its width is less than 2 mm. This low weight and the small dimensions make it possible to implant the micro plug-in connection in a human or lower animal without any problems. Also, the body does not evidence any rejection reactions after it is implanted.

A particularly compact construction of the device according to the invention is achieved by the outer sleeve, the central element, the spacers and the assembly elements being joined together with one another into a secure monolithic arrangement. This can be achieved by casting an adhesive or other polymeric material into the space or voids between the said sleeve, central element, spacers and assembly elements. In such an arrangement, the outer sleeve, the central element, and the spacers desirably are parallel to a common axis and have working or upper ends which lie in a plane lateral to the axis. Furthermore, the outer sleeve, the central element, and the spacers can be of equal length.

For better handling of the device according to the invention, it may also be provided with a handle.

If microcouplings (the female connector of a micro plug-in connection) comprising a plurality of coupling sleeves are to be produced by the device according to the invention, the assembly elements are preferably cylindrical assembly pins.

For producing a microplug (the male connector of a micro plug-in connection) comprising a plurality of plug elements with contact pins and plug sleeves, it is, on the other hand, preferable to design the assembly elements as cylindrical assembly bushes. However, it is also possible to use the assembly bushes to produce microcouplings (female connectors) having a plurality of coupling sleeves by placing coupling sleeves on assembly elements which are in the form of pins placed in the bushes.

In the case of a process for producing a microcoupling, comprising a plurality of coupling sleeves, using a device according to the invention, the coupling sleeves can be fitted onto cylindrical assembly elements in the form of pins and then aligned. Thereafter, the intermediate space between the coupling sleeves can be filled with an adhesive and the adhesive subsequently cured. After curing, the adhesively bonded coupling sleeves can be pulled off the assembly element pins thereby yielding a microcoupling.

If microplugs (male connectors) which comprise a plurality of plug elements with contact pins and plug sleeves (for attaching an electrical conductor) are to be produced by the device having the assembly bushes, the contact pins are inserted into the assembly bushes and the plug elements are aligned. The aligning can be made easier by fitting the coupling sleeves of an already finished microcoupling (female connector) onto the plug elements. Subsequently, the intermediate space between the plug sleeves can be filled with adhesive and the adhesive is cured. Thereafter, the adhesively bonded plug elements can be pulled off the assembly bushes thereby yielding a microplug.

The adhesive desirably is a dielectric adhesive, preferably an epoxy material such as Permapox ®, available from Permacol B.V., Abede, Netherlands.

The contact spacing of the coupling sleeves and plug elements should be at least 0.05 mm in order to prevent feed-over, or to achieve a dielectric strength of up to a maximum of 65 V d.c.

In the intermediate space between the plug elements or the coupling sleeves there may be provided, furthermore, a central bore for receiving a strain relief cord. The central bore preferably has two bore sections of different diameters, so that a strain relief line, such as a cord, thread, or filament, which may be formed for example of a Kevlar thread, is fed by one end through the bore section of smaller diameter and this end is knotted and subsequently adhesively bonded with a cyanoacrylate adhesive. As a result, when the strain relief line is subjected to tensile loading, the knot bears upon a ledge formed where the narrower diameter bore section ends and the wider diameter bore section begins.

In the case of an electric supply lead having at least one micro plug-in connection element, its contact elements are connected to electric conductors or wires. In order for this supply lead to be absolutely sealed and, in addition, also compatible with body tissue, the electric conductors and the micro plug-in connection element are surrounded by a continuous tubular casing or covering of polyurethane.

Any intermediate spaces between the tubular casing or covering and the micro plug-in connection element are filled with polyurethane adhesive.

While all of the components of the assembly device, the microplug, and the microcoupling are desirably made of a metal such as an alloy of copper and beryllium which is gold plated or copper gold plated, some components of the assembly device may be made of polymeric material.

A strain relief line is advantageously attached to the micro plug-in connection element and extended through the said element into the electric supply lead to prevent the element from being broken off of the supply lead.

If a gauze through and over which the skin of a patient can grow is attached to the polyurethane tube, tensile loading of the supply lead is not transferred directly to the instrument to which it is attached. In addition, relative movement between supply lead and skin is prevented, so that the incision in the skin through which the supply lead projects can heal. The gauze is readily bonded to the tube by means of a polyurethane adhesive. Such a gauze, for example, may be a netting of Mersilene ®, available from Ethicon GmbH, Norderstedt, Germany.

If in the case of this supply lead a micro plug-in connection element is attached at each end, this supply lead can remain when the implanted medical instrument is exchanged or replaced. A newly implanted instrument need only be fitted onto the micro plug-in connection element remaining in the body.

For this purpose, the supply lead attached to the instrument expediently likewise has a supply lead of which the micro plug-in connection element is surrounded by a polyurethane tube. At the point at which the two polyurethane tubes of the two micro plug-in connection elements (one male connector with pins and the other a female connector with pin receiving sleeves) butt against each other, they are bonded together with a polyurethane adhesive. In this way, a micro plug-in connection is produced which is absolutely sealed and compatible with body tissue.

BRIEF DESCRIPTION OF THE DRAWINGS

Specific embodiments of the invention are explained in more detail below with reference to the drawings, in which.

DETAILED DESCRIPTION OF THE DRAWINGS

Figure 1:
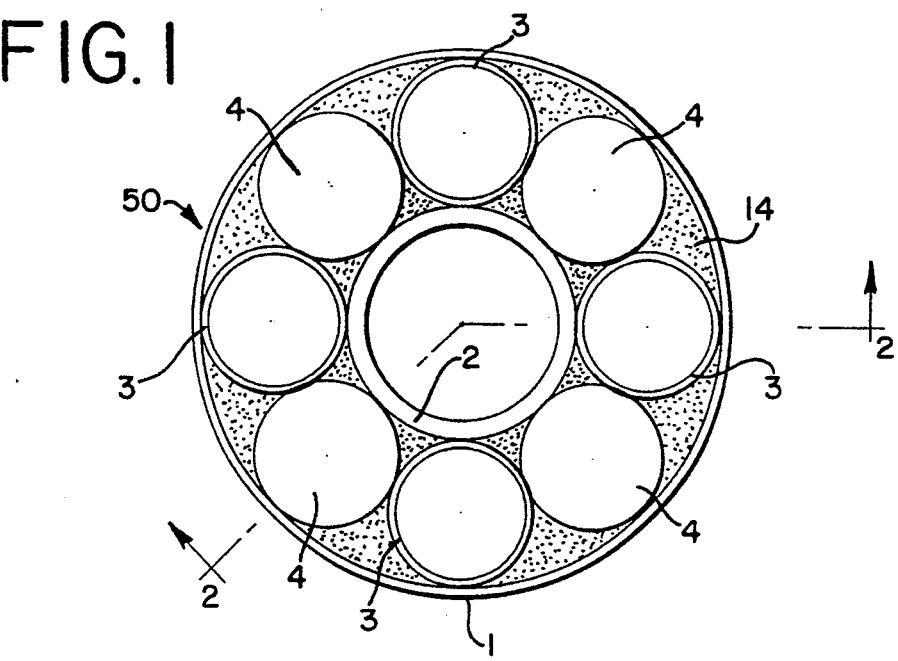
FIG. 1 is a plan view of a device having four assembly pins for producing a microcoupling (female connector) and which can also be used in a slightly modified form to produce a microplug (male connector)

The device 50 shown in FIG. 1 for producing a micro plug-in connection has a cylindrical outer sleeve 1, optionally provided with a handle 60, in which a central sleeve 2 in arranged coaxially thereto as a central element. In the intermediate space between the outer sleeve 1 and the central sleeve 2 there are alternately arranged four assembly pins 4 and four sleeve-shaped spacers 3. The outer sleeve 1, the central sleeve 2, the spacers 3, and the assembly pins 4 are parallel to a common axis. The upper or working ends of the outer sleeve 1, the central sleeve 2, and the spacers 3 are desirably positioned to lie in a plane lateral to said axis. The spacers 3 and the assembly pins 4 have the same outside diameter, which corresponds to the radial spacing between the outer surface of the central element 2 and the inner surface of the outer sleeve 1. The spacers 3 and the assembly pins 4 are accordingly respectively in contact with both the outer surface of the central sleeve 2 and the inner surface of the outer sleeve 1. The assembly pins 4 are also clamped-in in such a way that they are respectively in contact with the two neighboring or adjacent spacers 3.

To secure this arrangement, the intermediate space between the individual components 1, 2, 3 and 4 of the device 50 in FIG. 1 is filled with a synthetic casting or potting material 14, such as an adhesive or epoxy material.

Figure 2:
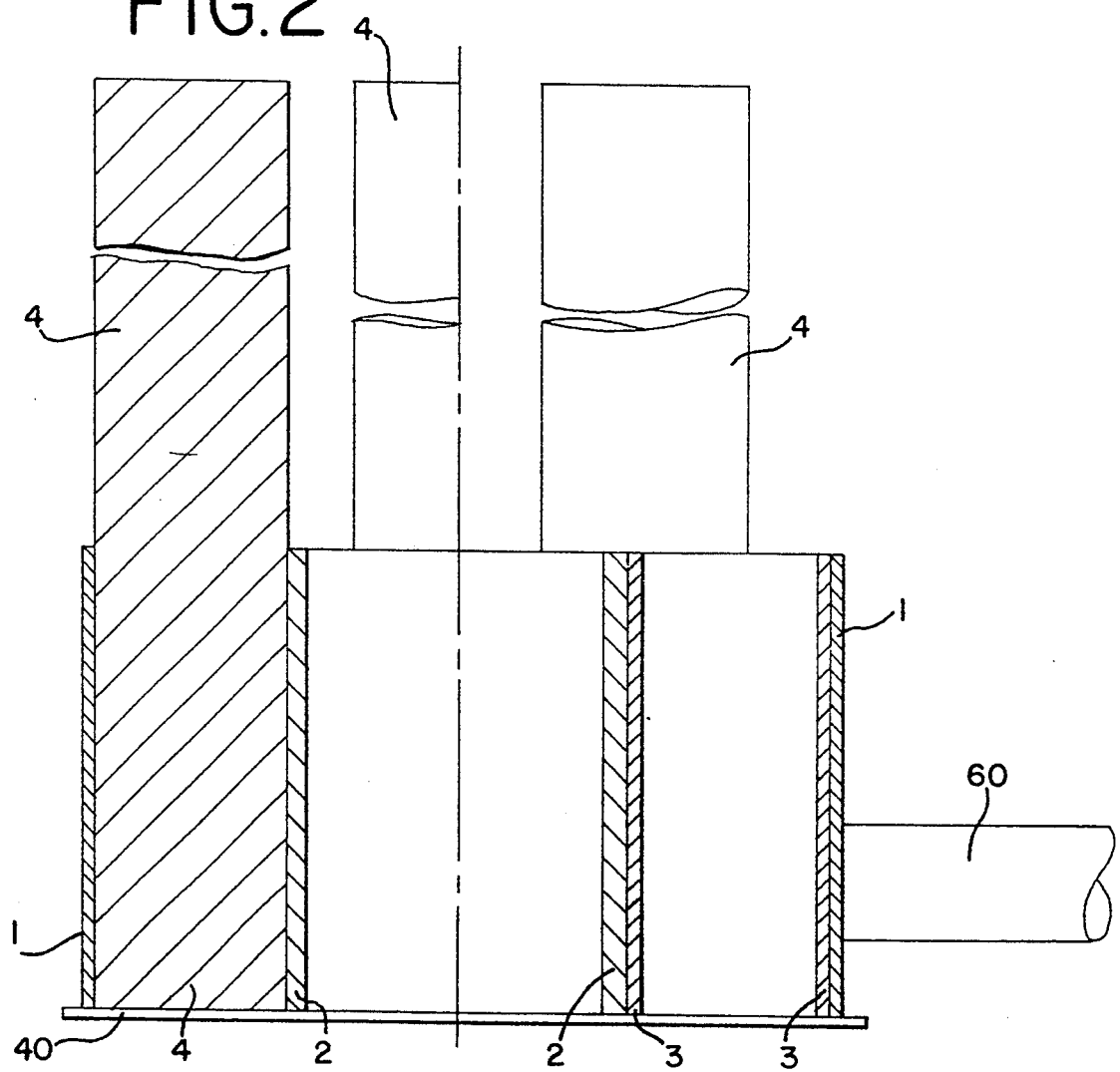
FIG. 2 is a sectional view taken along the line II—II of FIG. 1.
Figure 3:
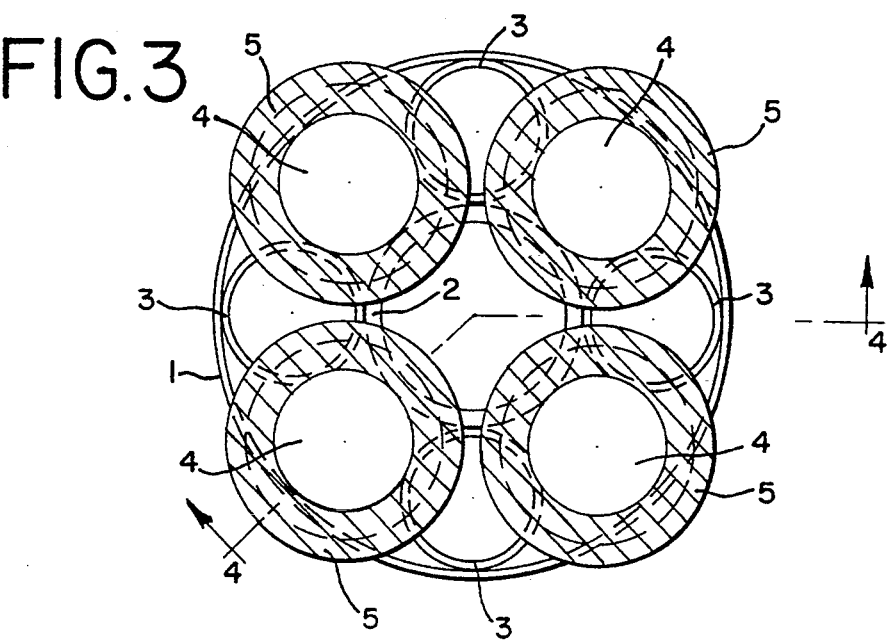
FIG. 3 illustrates the device of FIG. 1 in plan view with coupling sleeves arranged on it.
Figure 4:
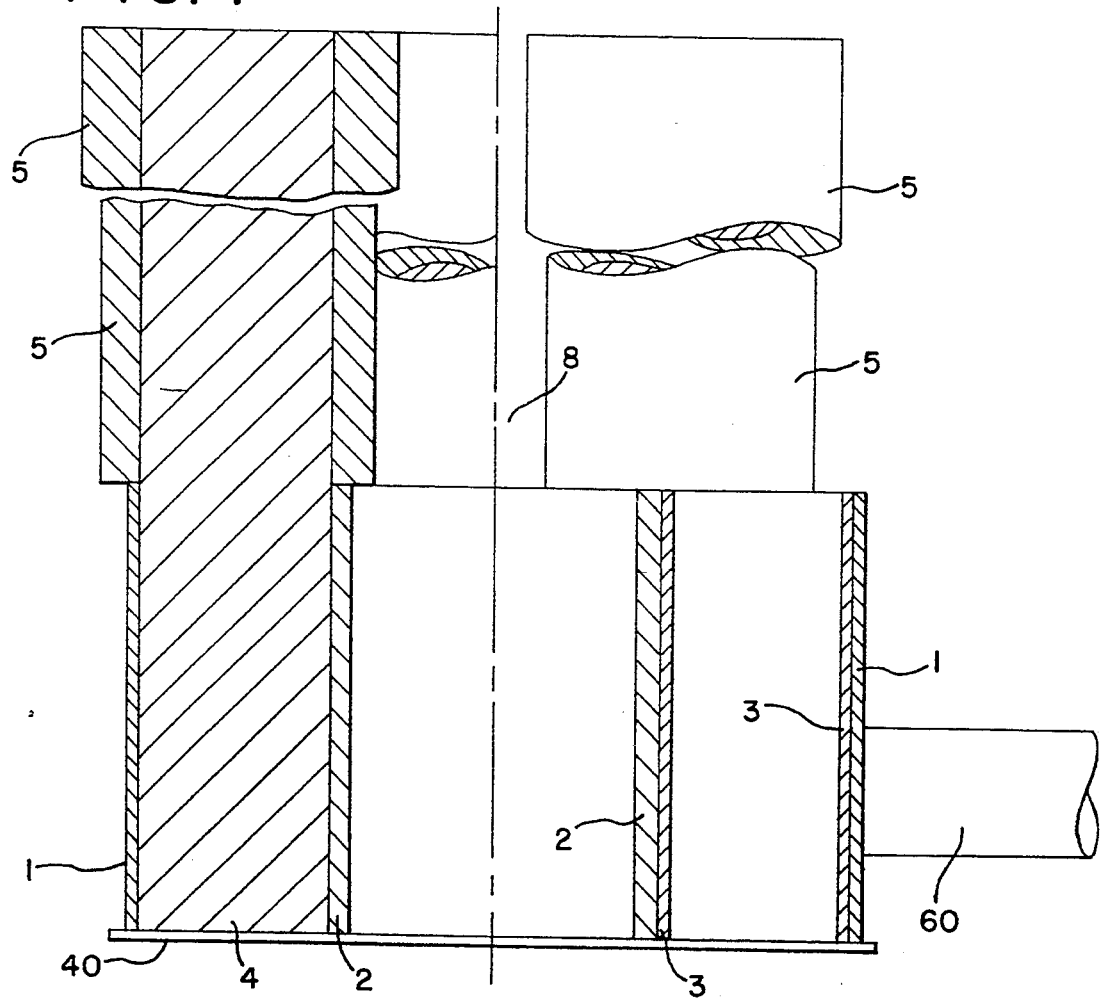
FIG. 4 is a sectional view taken along the line IV—IV of FIG. 3.

As can be seen from FIG. 2, the outer sleeve 1, the central sleeve 2 and the spacers 3 are of the same length but the assembly pins 4 extend or project upwardly are longer than those said other components. The assembly pins 4 are inserted in such a way that the bottom ends of these pins are flush with the bottom outer sleeve 1, the central sleeve 2 and the spacer 3. However, the upper end of the pins 4 project above the upper ends of all of sleeves 1 and 2 and spacer 3. The length by which the assembly pins project above the described arrangement of central sleeve 2, outer sleeve 1 and spacer 3 corresponds to the length of the microcoupling sleeves 5 (FIGS. 3 and 4) of a microcoupling to be produced, so that the microcoupling sleeves 5 are accommodated over their entire length by the assembly pins 4. An optional bottom plate 40 can be attached to the bottom of the assembly, if needed, to keep the components from sliding out.

To produce a microcoupling 30 (female connector) (FIGS. 3 to 6), four microcoupling sleeves 5, for example the coupling sleeve TC24S from Miles Roystone Ltd., Mansfield, Nottingham, England, are fitted onto the assembly pins 4 until they butt against the outer sleeve 1 and the central element 2. The inside diameter of the coupling sleeves 5 corresponds substantially to the outside diameter of the assembly pins 4.

The microcoupling sleeves 5 are subsequently aligned once again under a stereomicroscope. The intermediate space 8 (FIG. 4) between the microcoupling sleeves 5 is then filled, by means of a metering needle of a metering unit, with a dielectric adhesive 6 consisting of an epoxy resin casting or potting material, for example Permapox ®. The outer portion of the sleeves 5 remain essentially bare or uncoated by adhesive. The device is then cured for about three minutes under an infrared lamp at about 160° to 170° C. with simultaneous rotation of the device at about 60 revolutions per minute. After such curing, a central bore or hole 7 (FIGS. 6 and 8) is made in the intermediate space 8 between the individual coupling sleeves 5.

Figure 5:
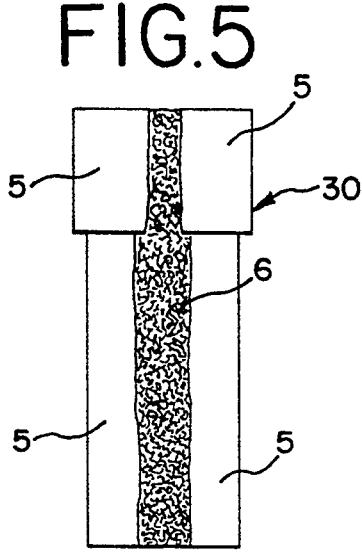
FIG. 5 is an elevational view of a microcoupling.
Figure 6:
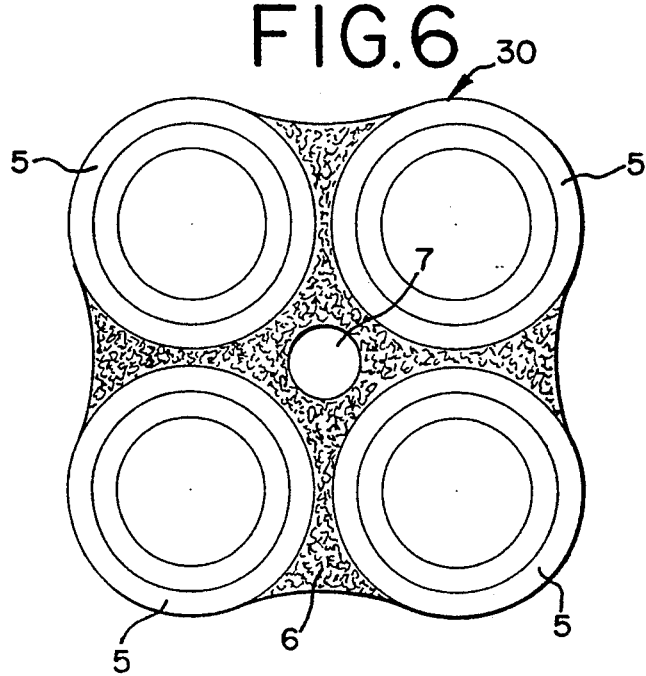
FIG. 6 is a plan view of the microcoupling shown in FIG. 5.

The microcoupling 30, after the epoxy resin casting has been finished, is shown in FIGS. 5 and 6.

Figure 7:
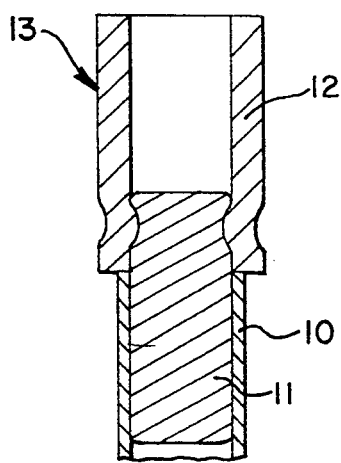
FIG. 7 is an elevational view of a microplug element inserted into an assembly bush for producing a microplug (male connector)

As is shown in FIG. 7, to produce a microplug (male connector), four assembly bushes 10 replace the assembly pins 4 in the device 50 (FIG. 1) for producing a microplug. The assembly bushes 10 are suitable for producing microplugs which comprise a plurality of four plug elements 13 which have a plug sleeve 12 and a projecting contact pin 11 attached therein. A plug element 13 which can be used is, for example, the plug element TC24P from Miles Roystone Ltd., Mansfield, Nottingham, England. The outside diameter of the contact pin 11 corresponds substantially to the inside diameter of the assembly bush 10.

For producing a microplug, the contact pins 11 are inserted into the openings of the assembly bushes 10 until the plug sleeve 12 butts against the assembly bush 10. The adhesive bonding or casting between and around the four plug sleeves 12 then takes place in the same way as the above-described casting between and around the coupling sleeves 5. The outer portion of the plug sleeve surfaces remains essentially bare or uncovered by adhesive. The microplug unitary assembly comprising the four bonded plug elements 13, each comprising a pin 11 and a plug sleeve 12, is subsequently pulled out of the assembly bushes 10.

It will be recognized that the device 50 shown in FIGS. 1 and 2 can be adapted to make microplugs in that the tubular spacers 3 can function as bushes 10 and the pins 4 when lowered to the height of external sleeve 1 can provide appropriate spacers for the bushes.

The device 50 when it has the four assembly bushes 10 for producing a microplug (male connector), can also be used to produce a microcoupling (female connector) of which the microcoupling sleeves 5 have an inside diameter which corresponds to the outside diameter of the assembly bushes 10.

Figure 8:
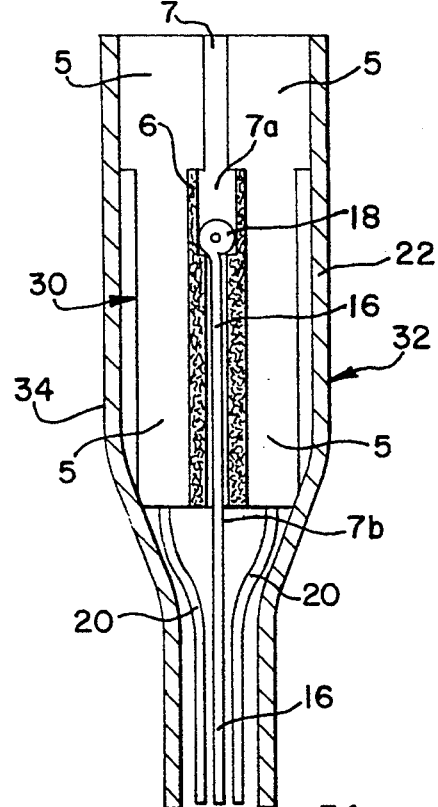
FIG. 8 is an elevational view, partially in cross-section, of one end of an electric supply lead joined to a microcoupling.

The supply lead shown in FIG. 8 has at its one end a microcoupling 30. The coupling sleeves 5 are in each case soldered at their terminal end to enamelled copper wires 20. For better flexibility, the four copper wires 20 may be twisted together, with the enamel layer insulating the copper wires 20 from one another.

The central bore 7 has two bore sections 7a, 7b. The bore section 7a adjoining the plug-in connection end of the microcoupling 30 has a larger diameter than the terminal-side bore section 7b.

From the terminal end, a Kevlar thread 16 is led from the top through the central bore 7. The end of the Kevlar thread 16 arranged in the bore section 7a is knotted 18 and bonded in place with cyanoacrylate adhesive. When the Kevlar thread 16 is subjected to tensile loading, the knot 18 bears against the ledge formed by the larger bore diameter 7a compared to the smaller bore diameter of section 7b.

The entire arrangement comprising microcoupling 30 (female connector), copper wires 20 and Kevlar thread 16 is surrounded by a polyurethane tube 22. In the region of the microcoupling 30, the polyurethane tube 22 is radially enlarged 34 and bears against the lower end of microcoupling 30 so that its lower end or face is flush with the lower end or face of the microcoupling 30. Any intermediate spaces between microcoupling 30 and polyurethane tube 22 are filled with cast-in-place solid polyurethane (not shown).

In the same way, a microplug 24 (male connector) (FIG. 9) can be attached at one end of the supply lead 32. The supply lead 32 comprises the four wires 20 inside of the polyurethane tube 22.

Figure 9:
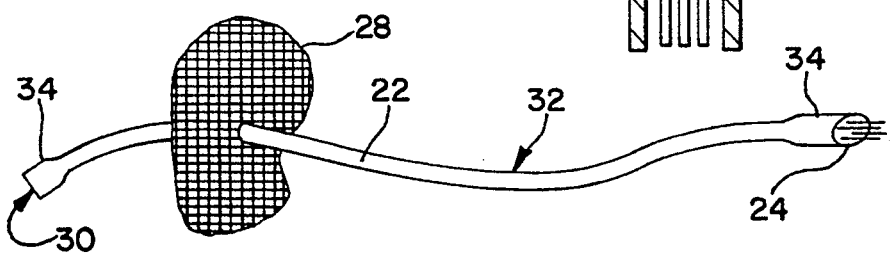
FIG. 9 illustrates a supply lead with a gauze through and over which skin can grow.

The supply lead 32 shown in FIG. 9 has a microcoupling 30 (female connector) at one end and a microplug 24 (male connector) at its other end. In the vicinity of the microcoupling 30 there is fastened a gauze 28 which is in the form of a circular netting and through and over which a patient's skin can grow. The gauze 28 is bonded to the polyurethane tube 22 by means of a polyurethane adhesive.

For attaching the supply lead 32 on the patient, the gauze 28 is implanted. The vibrovascular tissue then grows through the open netting and penetrates it. The supply lead 32 is then firmly connected to the skin.

To the end of the supply lead 32 located in the body of the patient a medical instrument, for example a cardiac catheter, may be electrically connected, and to it another supply lead of identical design as the supply lead 32 can be attached. The connection, at which the male and female ends of two coupled together polyurethane tubes 22 butt against each other, is bonded and covered with polyurethane adhesive for sealing purposes.

Securing of the supply lead 32 in place by the grownover gauze 28 ensures that the implanted instrument, such as a cardiac catheter, remains in its place when the supply lead 32 is subjected to tensile loading from outside the body.

The foregoing detailed description has been given for clearness of understand only, and no unnecessary limitations should be understood therefrom, as modifications will be obvious to those skilled in the art.

What is claimed is:

1. A device for producing a micro plug-in connection element, comprising:
   a cylindrical outer sleeve (1);
   a cylindrical central element (2) arranged coaxially in the outer sleeve (1);
   a plurality of cylindrical spacers (3) arranged between the outer sleeve (1) and the central element (2);
   a plurality of cylindrical assembly elements (4, 10), each of which is arranged between two neighboring spacers (3) and is in contact with the neighboring spacers (3), the central element (2) and the outer sleeve (1); and
   the assembly elements (4, 10) comprising a member of the group consisting of (A) assembly pins projecting beyond the arrangement comprising the outer sleeve, (1), central element (2) and spacers (3) and (B) bushes.

2. A device according to claim 1, in which:
   the outer sleeve (1), the central element (2) and the spacers (3) are essentially parallel to a common axis and they have adjacent ends which lie in a plane lateral to the axis.

3. A device according to claim 2 in which:
   the outer sleeve (1), the central element (2) and the spacers (3) are of essentially the same length.

4. A device according to claim 1 including:
   means monolithically bonding the outer sleeve (1), the central element (2), the spacers (3), and the assembly elements (4, 10) together.

5. A device according to claim 4 in which the means is a cast-in-place solid material which fills the space between and around the outer sleeve (1), the central element (2), the spacers (3), and the assembly elements (4, 10).

6. A device according to claim 1 in which:
   a handle is joined to the outer sleeve (1).

7. A device according to claim 1 in which:
   the assembly elements are assembly pins (4).

8. A device according to claim 1 in which:
   the assembly elements are assembly bushes (10).

* * * * *